United States Patent [19]

Greenbank et al.

[11] Patent Number: 4,465,875

[45] Date of Patent: Aug. 14, 1984

[54] PROCESS FOR DEHYDRATING ETHANOL

[75] Inventors: Michael Greenbank, Coraopolis; Michael R. Rosene, Pittsburgh, both of Pa.

[73] Assignee: Calgon Carbon Corporation, Pittsburgh, Pa.

[21] Appl. No.: 423,929

[22] Filed: Sep. 27, 1982

[51] Int. Cl.³ .................. C07C 29/77; C07C 31/08
[52] U.S. Cl. .................... 568/916; 44/53; 568/917
[58] Field of Search .................... 568/916, 917

[56] References Cited

U.S. PATENT DOCUMENTS

| | | | |
|---|---|---|---|
| 2,556,859 | 6/1951 | Vesterdal | 252/421 |
| 3,222,412 | 12/1965 | Mason et al. | 260/674 |
| 3,408,267 | 10/1968 | Miller et al. | 568/917 |
| 3,979,330 | 9/1976 | Munzner et al. | 252/445 |
| 4,046,709 | 9/1977 | Yuki | 252/421 |
| 4,273,621 | 6/1981 | Fornoff | 203/19 |
| 4,277,635 | 7/1981 | Oulman et al. | 568/916 |
| 4,287,089 | 9/1981 | Convers et al. | 252/414 |
| 4,359,592 | 11/1982 | Chao et al. | 568/916 |

FOREIGN PATENT DOCUMENTS 608796  5/1978  U.S.S.R. .................... 568/917

OTHER PUBLICATIONS

F. F. Hartline, Science 206 41 (1979).

Primary Examiner—J. E. Evans
Attorney, Agent, or Firm—Michael C. Sudal, Jr.; R. Brent Olsen

[57] ABSTRACT

Aqueous ethanol and other lower alkanol water mixtures may be dehydrated in the gas or liquid phase by using carbon molecular sieves. These sieves preferentially adsorb water and recovery of absolute ethanol or other absolute alkanol is achieved. Absolute ethanol produced from this process may be used in the manufacture of gasohol.

7 Claims, No Drawings

PROCESS FOR DEHYDRATING ETHANOL

BACKGROUND OF THE INVENTION

Ethanol is readily produced by fermentation processes, which yield dilute aqueous ethanol mixtures. However, the dehydration of ethanol from its aqueous mixtures by traditional distillation methods requires large amounts of heat energy. Beverage grade ethanol is usually produced as an azeotrope containing 5 percent water by weight. For use in motor fuels, especially, gasohol, the ethanol must be substantially anhydrous.

Various methods for producing anhydrous ethanol, suitable for use in motor fuels are reviewed in Hartline, "Lowering the Cost of Alcohol", *Science,* Vol. 206, 41–42 (1979). Hartline describes only one adsorption process; using zeolite molecular sieves to selectively remove water from aqueous ethanol.

Oulman et al., U.S. Pat. No. 4,277,635 describe the use of a crystalline silica polymorph (silicalite) for the adsorption of ethanol from an aqueous ethanol mixture followed by recovery of the adsorbed, dehydrated ethanol by passing carbon dioxide gas through the silicalite bed.

Fornoff, U.S. Pat. No. 4,273,621 describes a gas phase distillation dehydration process using crystalline zeolite molecular sieves, and a carbon dioxide gas stream as a drying aid. This patent teaches that zeolite sieves having a pore diameter of three Angstroms are useful, because other adsorbents such as molecular sieves, carbon, alumina and silica would in addition to adsorbing water, coadsorb the ethanol and the carbon dioxide drying aid.

Zeolite sieves have one major drawback when used for the adsorption of water. They require a great deal of heat energy for desorption of the trapped water (i.e. regeneration).

None of the prior art discussed above, nor any of the references cited therein, suggest that carbon molecular sieves will be useful for dehydrating aqueous lower alkanol mixtures. It has been discovered that carbon molecular sieves having an average effective pore diameter of from 2.0 to 5.0 Angstroms are suitable for producing absolute ethanol, from an aqueous ethanol mixture having up to 60 percent water by weight. Moreover, carbon sieves, unlike zeolite sieves, are easily regenerated by methods such as those described herein.

SUMMARY OF THE INVENTION

This invention is directed to the removal of water from aqueous mixtures of lower alkanols, by employing carbon molecular sieves.

Thus, there is provided a process for dehydrating aqueous lower alkanol mixtures which comprises passing said mixtures through carbon molecular sieves having an average effective pore diameter in the range of about 2.0 to 5.0 Angstroms.

DETAILED DESCRIPTION OF THE INVENTION

The term "lower alkanol," as used herein refers to those $C_2$ to $C_5$ straight and branched, generally saturated alcohols that form azeotropes with water. Examples include ethanol, n-propanol, isopropanol, n-butanol, sec-butanol, tert-butanol and sec-amyl alcohol. Methanol, is also to be included as a lower alkanol, but it does not azeotrope with water. The term "absolute" is defined as 100% and it refers to an alkanol containing no water.

The term "carbon molecular sieve" as used herein refers to those carbonaceous adsorbents that have been manufactured under conditions which control pore diameter. Typical carbon molecular sieves and processes for their production are described in Mason et al., U.S. Pat. No. 3,222,412; Munzner et al., U.S. Pat. No. 3,979,330; Yuki, U.S. Pat. No. 4,046,709 and Vesterdal, U.S. Pat. No. 2,556,859.

It is anticipated that any carbon molecular sieve having an average effective pore diameter of from about 2.0 Angstroms to about 5.0 Angstroms will be useful in this application. Pore diameters within this range allow water to be more readily adsorbed from a water-lower alkanol mixture than the alkanol.

The preferred method of dehydrating an aqueous lower alkanol mixture is by distillation. The azeotropic gaseous mixture of water and lower alkanol is distilled through a column of carbon molecular sieves having average effective pore diameters within the range of about 2.0 to 5.0, Angstroms and, for ethanol, preferably 2.5 to 3.5 Angstroms. The water vapor is preferentially adsorbed, and the dehydrated lower alkanol is recovered by condensation.

It is also anticipated that carbon molecular sieves will adsorb water from an aqueous lower alkanol mixture in the liquid phase. Employing standard adsorption techniques, a mixture of aqueous lower alkanol would be passed through a column of carbon molecular sieves, at a flow rate found to be sufficient to allow adequate adsorption by the carbon of the water in the mixture. Generally, a slow flow rate is preferred, for example, about 100 milliliters per hour. Repeated passages through carbon molecular sieve columns may be necessary depending upon the amount of water present and/or the degree of dryness desired.

After the carbon molecular sieves have become saturated with adsorbed water, they must be replaced with virgin carbon molecular sieves or be regenerated. Water may be removed from the carbon sieves by numerous known methods. One common method is to drive off the water by heating the carbon at a temperature sufficient to volatilize the adsorbed water and thereafter passing a dry carrier gas such as nitrogen or air through the sieve to aid in removing the water vapor. Another method for removing water from carbon is described in Convers et al., U.S. Pat. No. 4,287,089. This method employs 1,2-dichloroethane both in the liquid and gas phase to remove adsorbed water.

While the examples that follow are directed to the preferred embodiment of this invention, namely the dehydration of aqueous ethanol, nevertheless it is to be noted that the present invention is not limited solely to this preferred embodiment. Other aqueous lower alkanol solutions may be dehydrated using either a gas phase process or a liquid phase process as described herein without departing from the spirit of this invention. The carbon molecular sieve, NSC-4, has an average effective pore diameter of about 4 Angstroms and is available from Calgon Carbon Corporation, Pittsburgh, Pa.

EXAMPLE 1

A 100 ml sample of ethanol containing 9.0 weight percent water was distilled through a column containing about 70 grams of carbon molecular sieves. The resulting dehydrated ethanol was collected from a condenser and analyzed for its water content. The results were as follows:

| Fraction No. | Volume | % Ethanol |
|---|---|---|
| 1 | 5 ml | 100.0 |
| 2 | 25 ml | 97.0 |
| 3 | 30 ml | 95.0 |
| 4 | 25 ml | 95.0 |

EXAMPLE 2

A 100 ml sample of ethanol containing 20 weight percent water is distilled through a column containing about 150 grams of carbon molecular sieves. The resulting dehydrated ethanol is collected from a condenser and analyzed for its water content. The results are:

| Fraction No. | Volume | % Ethanol |
|---|---|---|
| 1 | 10 ml | 99.5 |
| 2 | 10 ml | 97.0 |
| 3 | 15 ml | 96.0 |
| 4 | 10 ml | 95.5 |
| 5 | 20 ml | 95.0 |
| 6 | 20 ml | 95.0 |
| 7 | 5 ml | 95.0 |

EXAMPLE 3

A 200 ml sample of ethanol containing 60 weight percent water is distilled through a column containing 250 g of carbon molecular sieves. The resulting dehydrated ethanol is collected from a condenser and analyzed for its water content. The results are:

| Fraction No. | Volume | % Ethanol |
|---|---|---|
| 1 | 2 ml | 100 |
| 2 | 2 ml | 99.5 |
| 3 | 5 ml | 99.0 |
| 4 | 5 ml | 99.0 |
| 5 | 5 ml | 99.0 |
| 6 | 5 ml | 98.5 |
| 7 | 10 ml | 98.0 |
| 8 | 15 ml | 98.0 |
| 9 | 15 ml | 97.0 |

EXAMPLE 4

A 100 ml sample of ethanol containing 10 weight percent water is passed through a column containing 250 grams of carbon molecular sieves at a flow rate of 100 ml/hour. The resulting dehydrated ethanol is analyzed for its water content. The results are:

| Fraction No. | Volume | % Ethanol |
|---|---|---|
| 1 | 2 ml | 100 |
| 2 | 2 ml | 99.5 |
| 3 | 5 ml | 99.0 |
| 4 | 11 ml | 99.0 |
| 5 | 15 ml | 99.0 |
| 6 | 10 ml | 99.0 |
| 7 | 10 ml | 98.5 |
| 8 | 10 ml | 98.5 |
| 9 | 20 ml | 98.0 |
| 10 | 4 ml | 97.5 |

Following the above examples, other dehydrated lower alkanols may be produced, including absolute butanol, absolute isopropanol, absolute sec-amyl alcohol and the like.

Claims to the invention follow.

What is claimed is:

1. A process for dehydrating aqueous lower alkanol mixtures which comprises:
   (a) passing said mixtures through carbon molecular sieves having average effective pore diameters within the range of about 2.0 to 5.0 Angstroms to adsorb the water onto said carbon molecular sieves; and subsequently
   (b) removing said water from said carbon molecular sieves.

2. The process of claim 1 wherein the average effective pore diameters for the carbon molecular sieves are from about 2.5 to 3.5 Angstroms.

3. The process of claim 1 which further comprises passing said aqueous lower alkanol mixtures through said carbon molecular sieves in the liquid phase.

4. The process of claim 1 which further comprises passing said aqueous lower alkanol mixtures through said carbon molecular sieves in the gaseous phase.

5. The process of claims 3 or 4 wherein the aqueous lower alkanol mixture is up to 60 weight percent water.

6. The process of claim 4 wherein an absolute lower alkanol is produced.

7. The process of claim 6 wherein the absolute lower alkanol produced is ethanol.

* * * * *